United States Patent [19]

Obayashi et al.

[11] Patent Number: 4,507,438
[45] Date of Patent: Mar. 26, 1985

[54] WATER-ABSORBENT RESIN HAVING IMPROVED WATER-ABSORBENCY AND IMPROVED WATER-DISPERSIBILITY AND PROCESS FOR PRODUCING SAME

[75] Inventors: Shigeji Obayashi, Akashi; Morio Nakamura, Kakogawa; Takushi Yamamoto, Kobe; Masato Fujikake, Kakogawa, all of Japan

[73] Assignee: Seitetsu Kagaku Co., Ltd., Hyogo, Japan

[21] Appl. No.: 448,150

[22] Filed: Dec. 9, 1982

[30] Foreign Application Priority Data

Dec. 30, 1981 [JP] Japan ................... 56-213885

[51] Int. Cl.$^3$ ................ C08L 3/02; C08L 9/00; C08L 31/04; C08L 33/06
[52] U.S. Cl. ................. 525/119; 525/54.31; 525/54.32; 525/116; 525/118; 525/125; 525/155; 527/306
[58] Field of Search ............... 525/118, 119, 143, 162, 525/163, 116, 123, 154, 54.31, 54.32, 125, 155; 527/306

[56] References Cited

U.S. PATENT DOCUMENTS 3,966,679 6/1976 Gross ................... 525/119
4,351,922 9/1982 Yoshida et al. .......... 525/119

FOREIGN PATENT DOCUMENTS 0036463 9/1981 European Pat. Off.
6674 10/1967 Japan.
51-136588 11/1976 Japan.

*Primary Examiner*—Allan M. Lieberman
*Attorney, Agent, or Firm*—Pollock, Vande Sande & Priddy

[57] ABSTRACT

Water-absorbent resins having improved water-absorbency, water-absorption rate and water-dispersibility can be produced by crosslinking a water-absorbent resin comprising a carboxylate as a constituent of the resin with a crosslinking agent having at least two functional groups in the presence of water in a proportion of 0.01 to 1.3 parts by weight per part by weight of the resin in an inert solvent.

16 Claims, No Drawings

WATER-ABSORBENT RESIN HAVING IMPROVED WATER-ABSORBENCY AND IMPROVED WATER-DISPERSIBILITY AND PROCESS FOR PRODUCING SAME

This invention relates to a water-absorbent resin having an improved dispersibility in water and an improved water-absorbency, and a process for producing the water absorbent resin. More particularly, it relates to a process for producing a water-absorbent resin having an improved water-absorbency and an improved water-dispersibility which comprises crosslinking a water-absorbent resin comprising a carboxylate as a constituent of the resin with a crosslinking agent having at least two functional groups in the presence of water in an inert solvent.

Water absorbent resins are used in the field of sanitation as menstrual articles, diaper, disposable house-cloth and the like and in the field of agriculture and horticulture as water retentive materials. Further, they are useful in other various fields such as coagulation of sludges, prevention of dew condensation on construction materials, dehydration of oils and so on. As this type of water-absorbent resin, there are known crosslinked carboxymethyl cellulose, partially crosslinked polyethylene oxide, crosslinked hydrolyzate of starch-acrylonitrile graft copolymer, partially crosslinked polyacrylic acid salt and the like. However, all of them have disadvantages that they have low water-absorbency, and even if the water-absorbency is satisfactory, the water-dispersibility is inferior or the water-absorbing rate is low.

If these disadvantages are overcome, it is clear that the water absorbent resins will be more broadly used in various fields including sanitary articles such as sanitary napkin, paper diaper, underpad, and the like, and it has been desired that improved articles come into the market.

As the water-absorbent resin, there are known various synthetic resins as mentioned above. Particularly, Japanese Patent Application Kokai (Laid-Open) Nos; 93,716/81; 131,608/81 and 147,806/81 disclose methods for producing water-absorbent resins using as the starting material acrylic acid, which are commercially easily available and are uniform in quality. These water-absorbent resins have an improved water-absorbency even in an aqueous electrolyte solution and an improved stability in the water-absorbed state. However, these water-absorbent resins are still unsatisfactory in dispersibility in water and water-absorbing rate. Moreover, European patent application No. 80304099.7 (Publication No. 0036463) and U.S. Pat. No. 4,340,706 disclose that a water-absorbent resin suitable for usages requiring a stability in the fluid-absorbed state for a long period of time or a high water-absorbing rate can be obtained by crosslinking an acrylic acid salt polymer with a crosslinking agent. However, even the resin obtained by said method is still not sufficient in water-dispersibility and water-absorption rate.

The present inventors have further made research on the conditions for crosslinking water-absorbent resins with a crosslinking agent. As a result, it has surprisingly and unexpectedly been found that when a water-absorbent resin comprising a carboxylate as its constituent is crosslinked with a crosslinking agent having at least two functional groups in the presence of a specific amount of water in an inert solvent, the water-dispersibility and the water-absorption rate can both be greatly improved while retaining its water-absorbency as it is.

According to this invention, there is provided a process for producing a water-absorbent resin having an improved water-absorbing rate and water-dispersibility, characterized by crosslinking a water-absorbent resin comprising a carboxylate as a constituent of the resin with a crosslinking agent having at least two functional groups in the presence of water in a proportion of 0.01 to 1.3 parts by weight per part by weight of the resin in an inert solvent.

The water-absorbent resins used in this invention may be any polymer or copolymer comprising a carboxylate as its constituent. Among the polymers or copolymers, there may preferably be used those comprising an alkali acrylate or an alkali methacrylate as their constituent and those comprising a carboxylate and a hydroxyl group as their constituents.

As said water-absorbent resin, there may be used crosslinked polyacrylic acid salts, crosslinked copolymers of acrylic acid salt and methacrylic acid salt, crosslinked saponification products of methylacrylate-vinylacetate copolymer, crosslinked saponification products of starch-ethyl acrylate graft copolymer, crosslinked starch-acrylic acid salt graft copolymer, crosslinked saponification products of starch-methyl methacrylate graft copolymer, crosslinked saponification products of starch-acrylamide graft copolymer, crosslinked saponification products of starch-acrylonitrile-2-acrylamide-2-methylpropane sulfonic acid graft copolymer, crosslinked saponification products of starch-acrylonitrile graft copolymer, crosslinked saponification products of starch-acrylonitrile-vinylsulfonic acid graft copolymer, polyethylene oxide crosslinked with acrylic acid, crosslinked sodium carboxymethyl cellulose and the like.

The water-absorbent resins comprising a carboxylate as its constituent can be produced by the methods disclosed in Japanese patent application Kokai (Laid-Open) Nos. 93,716/81; 131,608/81; and 147,806/81 as referred to above as well as the methods disclosed in Japanese patent publication Nos. 30,710/79; 37,994/79; and 46,200/78 and U.S. Pat. No. 4,041,228. Representative methods for producing the water-absorbent resins which may be used as the starting materials are as follows:

Method 1

An aqueous solution of acrylic acid and alkali acrylate is suspended in an alicyclic or aliphatic hydrocarbon solvent containing a surfactant having an HLB of 8 to 12 and polymerized in the presence of a water-soluble radical polymerization initiator.

Method 2

To the polymerization reaction product obtained by the same way as in Method 1 is added a polyfunctional compound which can react with the carboxyl group, for example, a water-soluble glycidyl ether compound, a haloepoxy compound, or a dialdehyde compound, and the resulting mixture is subjected to reaction, after which the reaction product is slightly crosslinked.

Method 3

An aqueous solution of acrylic acid and alkali acrylate is suspended in a mixed solvent of an alicyclic or aliphatic hydrocarbon and an aliphatic alcohol containing a surface active agent and then polymerized in the presence of a water-soluble radical polymerization catalyst.

Method 4

An aqueous solution of partically neutralized acrylic acid having a neutralization degree of 50 to 90% is suspended in an aliphatic ketone, and then polymerized in the presence of a water-soluble radical polymerization catalyst and a water-soluble high molecular weight dispersing agent.

Method 5

In a petroleum-based aliphatic hydrocarbon solvent is dispersed a more than 40% by weight aqueous alkali metal acrylate solution containing a water-soluble radical polymerization initiator in the presence of a sorbitan fatty acid ester having an HLB of 3 to 6 and the resulting suspension is subjected to polymerization in the absence of a crosslinking agent.

Method 6

An aqueous sodium acrylate polymer solution is mixed with a crosslinking agent which can react with the carboxylate, and the resulting mixture is heated and dried at 30° C. or more to form a water-absorbent sodium acrylate polymer.

Method 7

Starch and acrylic acid are subjected to solution polymerization in the presence of ammonium ceric nitrate solution, after which aqueous sodium hydroxide and a crosslinking agent are added thereto. The resulting translucent solution is heated and dried to form a water-absorbent resin.

Method 8

Vinyl acetate and methyl acrylate are subjected to emulsion polymerization, and the copolymer thus obtained is saponified with sodium hydroxide in a methanol-water mixed solvent, after which the saponification product is removed by filtration and dried.

Other methods than those mentioned above may be used for producing the water-absorbent resins to be used as the starting material in the process of this invention.

However, none of the resins produced by the above-mentioned methods exhibit sufficiently satisfactory water-dispersibility and water-absorption rate.

In this invention, in order to improve the performance of the above-mentioned conventional water-absorbent resins, a specific amount of water is allowed to be present in the water-absorbent resins. The effect of water, in this case, is greatly varied depending upon its used amount. Accordingly, in this invention, water must be used in a proportion of 0.01 to 1.3 parts by weight per part of the water-absorbent resin. If the amount of water is less than 0.01 part by weight, the resin becomes in the substantially non-swollen state and hence the reaction thereof with the crosslinking agent is difficult to proceed and requires a long period of time. Therefore, said amount is disadvantageous in industry. On the other hand, the amount of water used is more than 1.3 parts by weight, the resin becomes too much swollen, and hence, the subsequent crosslinking reaction proceeds to the interior of the resin particles, whereby the crosslinking density in the surface layer of the polymer particle becomes low, resulting in no improvement in water-dispersibility and water-absorption rate. When it is intended to enhance the water-dispersibility and water-absorption rate in this case, more crosslinking agent becomes required, which rather reduces extremely the water-absorbency of the resin. Therefore, the use of more than 1.3 parts by weight of water is not desirable.

In view of the above fact, a particularly preferable result is obtained when water is used in a proportion of 0.05 to 1.0 part by weight per part by weight of the water-absorbent resin.

The inert solvent used in this invention is a solvent which does not affect the water-absorbent resin at all, and includes, for example, lower alcohols, polyhydric alcohols, ketones, ethers, aliphatic hydrocarbons, aromatic hydrocarbons, alicyclic hydrocarbons, halogenated hydrocarbons and the like. As the lower alcohol, preferred are alcohols having 1 to 8 carbon atoms, such as methyl alcohol, ethyl alcohol, normal propyl alcohol, isopropyl alcohol, normal butyl alcohol, isobutyl alcohol, tertiary butyl alcohol, amyl alcohol, octyl alcohol and the like. As the polyhydric alcohol, preferred are ethylene glycol, propylene glycol, glycerine, diethylene glycol and the like, and as the ether, there may be used diethyl ether, dibutyl ether, dioxane, tetrahydrofuran and the like.

As the aliphatic hydrocarbon, there may be used n-pentane, n-hexane, n-heptane, ligroin and the like; as the aromatic hydrocarbon, there may be used benzene, toluene, xylene, chlorobenzene and the like, and as the alicyclic hydrocarbon, there may be used cyclopentane, methylcyclopentane, cyclohexane, methylcyclohexane, and the like. Further, the halogenated hydrocarbon includes carbon tetrachloride, methylene chloride, chloroform, ethylene dichloride, trichloroethylene and the like.

The above-mentioned inert solvents may be used alone or in admixture of two or more. However, in industry, the use of methyl alcohol, n-hexane, n-heptane or cyclohexane alone is more preferable.

The proportion of the inert solvent to the water-absorbent resin is preferably 0.1 to 50 parts by weight, more preferably 0.2 to 20 parts by weight, per part by weight of the water-absorbent resin, though it may be varied depending upon the kind of water-absorbent resin and the kind of the inert solvent. The smaller the amount of the inert solvent, the higher the volume efficiency. However, the dispersion of the water-absorbent resin becomes bad and the uniform crosslinking becomes difficult. On the contrary, when the amount of the inert solvent is larger, the water-absorbent resin tends to be dispersed and the crosslinking tends to take place uniformly. However, the volume efficiency becomes bad and the resin becomes difficult to handle. Therefore, the process of this invention must be carried out using water in an amount within the above-mentioned range.

As the crosslinking agent used in this invention, there may be used any crosslinking agent having at least two functional groups which can react with the carboxylate, or groups present in the polymer such as hydroxyl group, sulfonic acid group, amino group and the like, including diglycidyl ether compounds, haloepoxy compounds, aldehyde compounds, isocyanate compounds and the like. Among them, diglycidyl ether compounds are particularly preferred. Specific examples of the diglycidyl ether compounds are (poly)ethyleneglycol diglydicyl ether, (poly)propyleneglycol diglycidyl ether, (poly)glycerine diglycidyl ether and the like, among which ethylene glycol diglycidyl ether is most preferable. Examples of the haloepoxy compounds are epichlorohydrin, epibromohydrin, α-methylepichlorohydrin and the like, and examples of the aldehyde compounds are glutaraldehyde, glyoxal and the like, and examples of the isocyanate compounds are 2,4-tolylene diisocyanate, hexamethylene diisocyanate and the like. All of them may be used effectively in this invention. Such crosslinking agents are selected depending upon the kind of the water-absorbent resin, and the purpose of use thereof lies in imparting a crosslinked structure again to the resin having water-absorbency. Therefore, the amount of the crosslinking agent used is generally very slight, and may be varied depending upon the kind of crosslinking agent, the kind of inert solvent, the amount of water present, and the purpose of use of water-absorbent resin, though usually appropriate is the amount of 0.005 to 5.0% by weight based on the weight of the water-absorbent resin. In general, if the amount of the crosslinking agent used is less than 0.005% by weight, the effect of addition does not appear, and if the amount is more than 5.0% by weight, there is obtained a resin having an extremely high degree of crosslinking which reduces remarkably the water-absorbency. Therefore, such amounts are not desirable.

There may be used many methods for crosslinking the resin with a crosslinking agent in this invention. That is to say, the water-absorbent resin may be dispersed in an inert solvent, followed by adding water and then the crosslinking agent to the resulting dispersion, and thereafter heat-treating the resulting slurry, preferably under reflux, or alternatively, the slurry after the addition of the crosslinking agent may be heated and evaporated, to effect the crosslinking. As other methods, the reaction mixture obtained by the reaction in the presence of an inert solvent mentioned above may be subjected to adjustment of the ratio between the water-absorbent resin and the water, followed by adding a crosslinking agent and thereafter, heat-treating the resulting mixture, preferably under reflux, or alternatively, the slurry after the addition of the crosslinking agent may be heated and evaporated, to effect the crosslinking. The heat-treated product may be, of course, subjected to filtration and drying to obtain a commercial product.

In order to conduct the above-mentioned crosslinking reaction smoothly, the temperature for the heat-treatment of the slurry may preferably be usually within the range of from 40° to 150° C. though the temperature may be varied depending upon the kind of the crosslnking agent used, the kind of the inert solvent used, the amount of water present and the purpose of use of the water-absorbent resin and hence cannot be uniquely determined.

This invention is characterized in that the treatment method is simple, the formation of unswollen powder lump at the initial stage of water-absorption can be prevented, the dispersibility in water can greatly be improved and simultaneously the water-absorption rate is much enhanced as well as the workability in actual use in various fields can be improved.

This invention is further explained below in more detail referring to Examples and Comparative Examples. However, these Examples are merely by way of illustration and not by way of limitation.

The term "absorbency" used herein means a value determined according to the following procedure: In the case of deionized water-absorbency, 2 liters of deionized water and 1 g of the dried polymer were placed in a 3-liter beaker, and water was absorbed by the polymer for a predetermined period of time while the mixture was allowed to stand, after which the polymer was collected by filtration with a 100-mesh metallic wire gauze and the volume of the swollen polymer obtained as a filtered cake was measured by means of a messcylinder. The value was taken as the deionized water-absorbency.

In the case of saline solution-absorbency, 200 ml of saline solution (0.9% by weight aqueous sodium chloride solution) and 1 g of dried polymer were placed in a 300-ml beaker and the solution was absorbed by the polymer for the predetermined period of time while the mixture was allowed to stand, after which it was filtered with a 100-mesh metallic wire gauze, and the volume of the swollen polymer obtained as a filtered cake was measured by means of a messcylinder. The value was taken as the saline solution-absorbency.

COMPARATIVE EXAMPLE 1

In a 200-ml flask was placed 39.1 g of acrylic acid having a purity of 99.8% by weight, and 76.5 g of a 22.6% by weight aqueous sodium hydroxide solution was dropped thereinto with cooling and stirring to neutralize 80 mole % of the acrylic acid, after which 0.13 g of potassium persulfate was added thereto. The resulting mixture was stirred at room temperature to form a solution.

Into a 500-ml flask provided with a reflux condenser purged with nitrogen were charged 213 g of cyclohexane and 1.9 g of sorbitan monolaurate having an HLB of 8.6, after which a surfactant was dissolved at room temperature with stirring. To the resulting solution was added dropwise the above-mentioned aqueous partially neutralized acrylic acid solution to form a suspension. The flask was again sufficiently purged with nitrogen, the temperature of the suspension was elevated and polymerization was conducted for 3 hours while keeping the bath temperature at 55°-60° C.

The resulting polymerization mixture was vaporized to dryness under reduced pressure, to obtain 48.0 g of fine, granular, dried polymer. The water-absorbency and saline solution-absorbency of the polymer were as shown in Table 3.

COMPARATIVE EXAMPLE 2

In a 100-ml flask was placed 39.1 g of acrylic acid having a purity of 99.8% by weight, and 54.2 g of a 28% by weight aqueous sodium hydroxide solution was dropped thereinto with cooling and stirring to neutralize 70 mole % of the acrylic acid, after which 0.13 g of potassium persulfate was added thereto. The resulting mixture was stirred to form a solution at room temperature.

In a 500-ml flask provided with a stirrer purged with nitrogen were placed 213.6 g of cyclohexane and 1.1 g of sorbitan monostearate, and the surfactant was dissolved at 50°-55° C. with stirring. The resulting solution was cooled to room temperature, and the above-mentioned partially neutralized acrylic acid solution was dropped thereinto to form a suspension. The temperature of the suspension was elevated with stirring while keeping the system at a reduced pressure of 300 Torr, and the suspension was kept at 50° C. to conduct the polymerization for 6 hours, after which the refluxing was stopped and the reaction mixture was evaporated to dryness under reduced pressure, thereby obtaining 48.8 g of a fine powder of white dried polymer. The water-absorbency and saline solution-absorbency of the polymer were as shown in Table 3.

COMPARATIVE EXAMPLE 3

Into a reactor provided with a stirrer, a nitrogen-blowing tube and a thermometer were charged 20 g of corn starch and 400 g of water, and the resulting mixture was stirred at 80° C. for one hour under a nitrogen atmosphere. The resulting aqueous solution was cooled to 30° C., and 60 g of acrylic acid and 30 g of ammonium ceric nitrate solution (0.1 mole of cerium ion in 1 N nitric acid) were added thereto, after which the resulting mixture was subjected to polymerization at 30°–40° C. for 3 hours.

To the polymerization mixture was added 50 g of a 30% by weight aqueous sodium hydroxide solution with stirring, and subsequently, 0.5 g of ethylene glycol diglycidyl ether was added thereto, after which the resulting mixture was poured into a tray, and dried at 100° C. for 3 hours and then at 60° C. for 2 hours under reduced pressure. The resulting sheet-shaped material was pulverized to obtain 95 g of white powder. The water-absorbency and saline solution-absorbency were as shown in Table 3.

COMPARATIVE EXAMPLE 4

In 300 ml of water containing 3 g of polyvinyl alcohol and 10 g of sodium chloride were dispersed 60 g of vinyl acetate and 40 g of methyl acrylate, and 0.5 g of benzoyl peroxide was added thereto, after which the resulting mixture was subjected to suspension polymerization at 65° C. for 6 hours. The resulting copolymer was separated by filtration and dried.

Subsequently, 34.4 g of the copolymer thus obtained was suspended in a saponifying solution consisting of 800 g of methanol, 40 g of water and 160 ml of 5 N aqueous sodium hydroxide solution, and the resulting suspension was subjected to saponification at 25° C. for one hour, after which the temperature of the saponification product was elevated to continue the saponification for 5 hours. After the completion of the saponification, the saponification product was washed well with methanol, and thereafter dried to obtain 26 g of a water-absorbent copolymer. The water-absorbency and saline solution-absorbency of the polymer were as shown in Table 3.

COMPARATIVE EXAMPLE 5

The same procedure as in comparative Example 1 was repeated, except that the 39.1 g of acrylic acid having a purity of 99.8% by weight was replaced by 35.2 g of acrylic acid having a purity of 99.8% by weight and 4.7 g of methacrylic acid having a purity of 99% by weight, to obtain 49.3 g of finely granular, dried polymer. The water-absorbency and saline solution-absorbency of the polymer were as shown in Table 3.

EXAMPLE 1

In a 500-ml flask provided with a stirrer, an oil bath and a cooler was placed 41 g of the water-absorbent resin having a water content of 2.5% obtained in the same manner as in Comparative Example 1, and 50 g of methanol was then added thereto, after which a solution of 32 mg of ethylene glycol diglycidyl ether in 9 g of water (total amount of water: 10 g) was added thereto with stirring. The resulting mixture was well stirred and then evaporated to dryness by keeping the oil bath at 110° C., to obtain 41.5 g of finely granular, dried polymer. The water-absorbency and saline solution-absorbency of the polymer were as shown in Table 3.

EXAMPLES 2–6

The same procedure as in Example 1 was repeated, except that the amounts of methanol and water were varied as shown in Table 1, to obtain finely granular, dried polymers. The water-absorbency and saline solution-absorbency of the polymers were as shown in Table 3.

TABLE 1

| Example No. | Methanol (g) | Water (g) | Total water (g) |
|---|---|---|---|
| 2 | 90 | 2.3 | 3.3 |
| 3 | 148 | 11.0 | 12.0 |
| 4 | 10.3 | 5.9 | 6.9 |
| 5 | 32 | 7.0 | 8.0 |
| 6 | 88 | 31.0 | 32.0 |

EXAMPLE 7

The same procedure as in Example 1 was repeated, except that the methanol was replaced by n-heptane, to obtain finely granular, dried polymer. The water-absorbency and saline solution-absorbency of the polymer were as shown in Table 3.

EXAMPLES 8–10

The same procedure as in Example 7 was repeated, except that the amount of ethylene glycol diglycidyl ether was varied as shown in Table 2, to obtain finely glanular, dried polymer. The water-absorbency and saline solution-absorbency of the polymer were as shown in Table 3.

TABLE 2

| Example No. | Ethyleneglycol diglycidyl ether (mg) |
|---|---|
| 8 | 10 |
| 9 | 100 |
| 10 | 500 |

EXAMPLE 11

The same procedure as in Example 1 was repeated, except that epichlorohydrin was substituted for the ethylene glycol diglycidyl ether, to obtain finely granular, dried polymer. The water-absorbency and saline solution-absorbency of the polymer were as shown in Table 3.

EXAMPLE 12

From the polymerization mixture obtained in Comparative Example 2 was removed 22.2 g of the water and subsequently, 47.4 mg of ethylene glycol diglycidyl ether was added thereto, after which the resulting mixture was well stirred. The oil bath was thereafter kept at 110° C. to evaporate the mixture to dryness, thereby obtaining finely divided, dried polymer. The water-absorbency and saline solution-absorbency of the polymer were as shown in Table 3.

EXAMPLE 13

The same procesure as in Example 1 was repeated, except that the water-absorbent resin obtained in the same manner as in Comparative Example 3 was substituted for the water-absorbent resin and polyethylene glycol diglycidyl ether was substituted for the ethylene glycol diglycidyl ether, to obtain powdery, dried polymer. The water-absorbency and saline solution-absorbency of the polymer were as shown in Table 3.

EXAMPLE 14

The same procedure as in Example 1 was repeated, except that the water-absorbent resin obtained in the same manner as in Comparative Example 4 was substituted for the water-absorbent resin, and glycerine diglycidyl ether was substituted for the ethylene glycol diglycidyl ether, to obtain finely granular, dried polymer. The water-absorbency and saline solution-absorbency of the polymer were as shown in Table 3.

EXAMPLE 15

The same procesure as in Example 1 was repeated, except that the water-absorbent resin obtained in the same manner as in Comparative Example 5 was substituted for the water-absorbent resin, to obtain finely granular, dried polymer. The water-absorbency and saline solution-absorbency of the polymer were as shown in Table 3.

COMPARATIVE EXAMPLE 6

The same procedure as in Example 1 was repeated, except that 100 g of n-heptane and 59 g of water were substituted for the methanol, to obtain a lump-like, dried polymer, which was then pulverized and used to measure the water-absorbency and saline solution-absorbency. The results obtained were as shown in Table 3.

TABLE 3

| | Amount of water present (% by weight) | Solvent Kind | Solvent Amount (% by wt.) | Water-absorbent resin (% by wt.) | Water/resin weight ratio | Crosslinking agent Kind | Crosslinking agent Amount (mg) |
|---|---|---|---|---|---|---|---|
| Comp. Ex. 1 | — | — | — | — | — | — | — |
| Comp. Ex. 2 | — | — | — | — | — | — | — |
| Comp. Ex. 3 | — | — | — | — | — | — | — |
| Comp. Ex. 4 | — | — | — | — | — | — | — |
| Comp. Ex. 5 | — | — | — | — | — | — | — |
| Example 1 | 10 | Methanol | 50 | 40 | 0.25 | E-100 | 32 |
| Example 2 | 2.5 | " | 67.5 | 30 | 0.083 | " | " |
| Example 3 | 6.0 | " | 74 | 20 | 0.3 | " | " |
| Example 4 | 12 | " | 18 | 70 | 0.17 | " | " |
| Example 5 | 10 | " | 40 | 50 | 0.2 | " | " |
| Example 6 | 20 | " | 55 | 25 | 0.8 | " | " |
| Example 7 | 10 | n-Heptane | 50 | 40 | 0.25 | " | " |
| Example 8 | 10 | " | 50 | 40 | 0.25 | " | 10 |
| Example 9 | 10 | " | 50 | 40 | 0.25 | " | 100 |
| Example 10 | 10 | " | 50 | 40 | 0.25 | " | 500 |
| Example 11 | 10 | Methanol | 50 | 40 | 0.25 | ECH | 32 |
| Example 12 | 8.34 | Cyclohexane | 75.03 | 16.63 | 0.50 | E-100 | 47.4 |
| Example 13 | 10 | Methanol | 50 | 40 | 0.25 | E-400 | 32 |
| Example 14 | 10 | " | 50 | 40 | 0.25 | E-100 | 32 |
| Example 15 | 10 | " | 50 | 40 | 0.25 | E-100 | 32 |
| Comp. Ex. 6 | 30 | n-Heptane | 50 | 20 | 1.50 | E-100 | 32 |

| | Deionized water-absorbency (ml/g) After 1 min | Deionized water-absorbency (ml/g) After 5 min | Deionized water-absorbency (ml/g) After 10 min | Saline solution-absorbency (ml/g) After 1 min | Saline solution-absorbency (ml/g) After 5 min | Saline solution-absorbency (ml/g) After 10 min | Formation of unswollen powder lump |
|---|---|---|---|---|---|---|---|
| Comp. Ex. 1 | 17 | 44 | 132 | 2 | 5 | 11 | Formed |
| Comp. Ex. 2 | 60 | 100 | 200 | 8 | 15 | 25 | " |
| Comp. Ex. 3 | 100 | 150 | 180 | 9 | 25 | 30 | A little formed |
| Comp. Ex. 4 | 80 | 200 | 420 | 8 | 20 | 41 | " |
| Comp. Ex. 5 | 150 | 230 | 520 | 10 | 24 | 31 | Formed |
| Example 1 | 670 | 950 | 1250 | 55 | 80 | 110 | None |
| Example 2 | 330 | 460 | 1100 | 31 | 65 | 98 | " |
| Example 3 | 650 | 930 | 1270 | 57 | 73 | 104 | " |
| Example 4 | 550 | 860 | 1180 | 56 | 75 | 105 | " |
| Example 5 | 600 | 910 | 1230 | 57 | 84 | 101 | " |
| Example 6 | 680 | 690 | 710 | 58 | 60 | 63 | " |
| Example 7 | 640 | 920 | 1300 | 54 | 77 | 116 | " |
| Example 8 | 320 | 640 | 950 | 32 | 63 | 90 | " |
| Example 9 | 650 | 970 | 1230 | 60 | 81 | 105 | " |
| Example 10 | 550 | 570 | 610 | 59 | 65 | 66 | " |
| Example 11 | 640 | 900 | 1080 | 53 | 74 | 98 | " |
| Example 12 | 480 | 520 | 540 | 51 | 55 | 56 | " |
| Example 13 | 160 | 170 | 190 | 20 | 31 | 33 | " |
| Example 14 | 300 | 410 | 670 | 18 | 41 | 50 | " |
| Example 15 | 700 | 1050 | 1390 | 63 | 86 | 122 | " |
| Comp. Ex. 6 | 70 | 170 | 230 | 6 | 18 | 24 | Formed |

Note:
E-100: Ethylene glycol diglycidyl ether
E-400: Polyethylene glycol diglycidyl ether
ECH: Epichlorohydrin
G-100: Glycerine diglycidyl ether

What is claimed is:
1. A process for producing a water-absorbent resin having an improved water-absorbency, characterized by crosslinking a crosslinked carboxylate-containing water-absorbent resin wherein said resin is acrylate homopolymer, acrylate copolymer, methacrylate ho- mopolymer, or methacrylate copolymer with 0.005–5% by weight of a crosslinking agent having at least two functional groups capable of reacting with a reactive group of said resin wherein said reactive group is selected from the class of carboxylate, hydroxyl, sulfonic acid, and amino in the presence of water in a proportion of 0.01 to 1.3 parts by weight per part by weight of the resin in 0.1 to 50 parts by weight, per part by weight of said resin of an invert solvent which does not affect the water-absorbent resin.

2. A process according to claim 1, wherein the water-absorbent resin is a polymer comprising an alkali acrylate or methacrylate as a constituent.

3. A process according to claim 1, wherein the water is present in a proportion of 0.05 to 1.0 parts by weight per part by weight of the water-absorbent resin.

4. A process according to claim 1, wherein the inert solvent is used in a proportion of 0.2 to 20 parts by weight per part by weight of the water-absorbent resin.

5. A process according to claim 1, wherein the inert solvent is methanol.

6. A process according to claim 1, wherein the inert solvent is cyclohexane.

7. A process according to claim 1, wherein the inert solvent is n-heptane.

8. A process according to claim 1, wherein the crosslinking agent is a diglycidyl ether compound.

9. A process according to claim 8, wherein the crosslinking agent is ethylene glycol diglycidyl ether.

10. A water-absorbent resin having an improved water-absorbency obtained by the process according to claim 1.

11. The process of claim 1 wherein said crosslinking agent is selected from the group of diglycidyl ether compounds, haloepoxy compounds, aldehyde compounds, and isocyanate compounds.

12. The process of claim 1 wherein said water-absorbent resin is selected from the group of polyacrylic acid salts, copolymers of acrylic acid salt and methacrylic acid salt, saponification products of methylacrylate-vinyl acetate copolymer, saponification products of starch-ethylacrylate graft copolymer, starch-acrylic acid salt graft copolymer, and saponification products of starch-methyl methacrylate graft copolymer.

13. The process of claim 1 wherein said water-absorbent resin is an acrylate homopolymer or copolymer.

14. The process of claim 1 wherein said crosslinking agent is a diglycidyl ether compound and said water-absorbent resin is an acrylic homopolymer or copolymer.

15. The process of claim 1 wherein the crosslinking is carried out while said resin is in dispersion form.

16. The process of claim 14 wherein said resin is a polyacrylic acid salt.

* * * * *

UNITED STATES PATENT AND TRADEMARK OFFICE
CERTIFICATE OF CORRECTION

PATENT NO. : 4,507,438
DATED : March 26, 1985
INVENTOR(S) : Obayashi, et al.

It is certified that error appears in the above-identified patent and that said Letters Patent is hereby corrected as shown below:

Column 2, line 13 before the word "polymer", insert the word --- crosslinked ---.

Signed and Sealed this

Twenty-seventh Day of August 1985

[SEAL]

Attest:

DONALD J. QUIGG

Attesting Officer

Acting Commissioner of Patents and Trademarks